United States Patent
Park et al.

(10) Patent No.: US 9,096,860 B2
(45) Date of Patent: Aug. 4, 2015

(54) MUTANTS HAVING CAPABILITY TO PRODUCE 1, 4-BUTANEDIOL AND METHOD FOR PREPARING 1, 4-BUTANEDIOL USING THE SAME

(75) Inventors: Si-Jae Park, Daejeon (KR); Sang-Hyun Lee, Daejeon (KR); Sang-Yup Lee, Daejeon (KR); Eun-Jeong Lee, Daejeon (KR)

(73) Assignees: LG CHEM, LTD., Seoul (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 692 days.

(21) Appl. No.: 12/676,840

(22) PCT Filed: Aug. 13, 2008

(86) PCT No.: PCT/KR2008/004700
§ 371 (c)(1),
(2), (4) Date: Aug. 9, 2010

(87) PCT Pub. No.: WO2009/031766
PCT Pub. Date: Mar. 12, 2009

(65) Prior Publication Data
US 2010/0330634 A1    Dec. 30, 2010

(30) Foreign Application Priority Data

Sep. 7, 2007    (KR) .................. 10-2007-0091081

(51) Int. Cl.
| | |
|---|---|
| *C12N 1/20* | (2006.01) |
| *C12P 7/18* | (2006.01) |
| *C12N 15/00* | (2006.01) |
| *C07H 21/04* | (2006.01) |
| *C12N 15/77* | (2006.01) |

(52) U.S. Cl.
CPC .. *C12N 15/77* (2013.01); *C12P 7/18* (2013.01)

(58) Field of Classification Search
CPC ............ C12P 7/46; C12P 19/04; C12P 7/065; C12P 7/18; C12R 1/00; C12N 1/20; C12N 9/0006; C12N 15/52; C12N 9/1029; C12N 1/32

See application file for complete search history.

(56) References Cited

U.S. PATENT DOCUMENTS

| | | | |
|---|---|---|---|
| 6,117,658 A | 9/2000 | Dennis et al. | |
| 2009/0047719 A1 * | 2/2009 | Burgard et al. | ............... 435/158 |

FOREIGN PATENT DOCUMENTS

| | | |
|---|---|---|
| KR | 10-2006-0011345 | 2/2006 |
| KR | 10-2007-0096348 | 10/2007 |
| WO | WO 2005/052135 | 6/2005 |

OTHER PUBLICATIONS

Lee et al. Metabolic engineering of *Escherichia coli* for enhanced production of succinic acid, based on genome comparison and in silico gene knockout simulation, Appl. and Environ. Microbiol. (2005), 71: 7880-7887.*
Engel et al. Transport of C4 dicarboxylates by anaerobically grown *E. coli* energetics and mechanism of exchange, uptake and efflux, Eur. J. Biochem. 222, 605-614 (1994).*
GenBank Accession No. AF321779, "*Clostridium acetobutylicum* plasmid pSOL1 aldehyde/alcohol dehydrogenase (adhE2) gene, complete cds", Jan. 17, 2002.
GenBank Accession No. X72831, "*C.acetobutylicum* adhE, ctfA and ctfB genes", Jun. 12, 2006.

* cited by examiner

*Primary Examiner* — Iqbal H Chowdhury
(74) *Attorney, Agent, or Firm* — McKenna Long & Aldridge LLP

(57) ABSTRACT

A mutant capable of producing 1,4-butanediol and a method of preparing 1,4-butanediol using the same are provided. The mutant microorganism is prepared by introducing and amplifying genes encoding enzymes converting succinate into 4-hydroxybutyrate and 4-hydroxybutyrate into 1,4-butanediol in a microorganism capable of producing succinate. The method includes culturing the mutant in a medium containing carbohydrate and obtaining 1,4-butanediol from the culture. Thus, 1,4-butanediol, which is essential in chemical industry, can be prepared in a biological process.

20 Claims, 3 Drawing Sheets

SEQUENCE LISTING

<160> NUMBER OF SEQ ID NOS: 23

<210> SEQ ID NO 1
<211> LENGTH: 1617
<212> TYPE: DNA
<213> ORGANISM: Unknown
<220> FEATURE:
<223> OTHER INFORMATION: Cat1-coding gene

<400> SEQUENCE: 1

| | | | | | |
|---|---|---|---|---|---|
| atgagtaaag | ggataaagaa | ttcacaattg | aaaaaaaaga | atgtaaaggc | tagtaatgtg | 60 |
| gcagaaaaga | ttgaagagaa | agttgaaaaa | acagataagg | ttgttgaaaa | ggcagctgag | 120 |
| gttactgaaa | aacgaattag | aaacttgaag | cttcaggaaa | aagttgtaac | agcagatgtg | 180 |
| gcagctgata | tgatagaaaa | cggtatgatt | gttgcaatta | gcggatttac | tccttccggg | 240 |
| tatcctaaag | aagtacctaa | agcattgact | aaaaaagtta | atgccttaga | ggaagaattc | 300 |
| aaggtaacac | tttatacagg | ttcatctaca | ggagccgata | tagacggaga | atgggcaaaa | 360 |
| gcaggaataa | tagaaagaag | aattccatat | cagacaaatt | ctgatatgag | gaaaaaaata | 420 |
| aatgatggtt | ctattaagta | tgctgatatg | catttaagcc | atatggctca | atatattaat | 480 |
| tattctgtaa | ttcctaaagt | agatatagct | ataatagagg | cagtagctat | tacagaagaa | 540 |
| ggggatatta | ttccttcaac | aggaattgga | aatacagcta | cttttgtgga | aaatgcagat | 600 |
| aaggtaatag | tggaaattaa | tgaggctcaa | ccgcttgaat | tggaaggtat | ggcagatata | 660 |
| tatacattaa | aaaaccctcc | aagaagagag | cccatacctg | tagttaatgc | aggcaatagg | 720 |
| atagggacca | catatgtgac | ctgtggttct | gaaaaaatat | gcgctatagt | gatgacaaat | 780 |
| acccaggata | aaacaagacc | tcttacagaa | gtgtctcctg | tatctcaggc | tatatccgat | 840 |
| aatcttatag | gattttttaaa | taagagggtt | gaagagggaa | aattacctaa | gaacctgctt | 900 |
| cctatacagt | caggagttgg | aagtgtagca | atgcagtttt | ggccggact | ttgtgaatca | 960 |
| aatttttaaaa | atttgagttg | ttatacagaa | gttatacagg | attctatgct | gaagcttata | 1020 |
| aaatgtggta | agcagatgt | ggtgtcaggc | acttccataa | gtccttcacc | ggagatgttg | 1080 |
| cctgagttca | taaaggacat | aaatttcttt | agagaaaaga | tagtattaag | accacaggaa | 1140 |
| ataagtaata | atccagagat | agcaagaaga | ataggagtta | tatccataaa | cactgctttg | 1200 |
| gaagtagata | tatatggtaa | tgtaaactcc | actcatgtta | tgggaagcaa | aatgatgaat | 1260 |
| ggtataggcg | gttctggaga | ctttgccaga | aatgcatatt | tgactatatt | cactacagag | 1320 |
| tctatcgcca | aaaaaggaga | tatatcatct | atagttccta | tggtatccca | tgtggatcat | 1380 |
| acagaacatg | atgtaatggt | aattgttaca | gaacagggag | tagcagattt | aagaggtctt | 1440 |
| tctcctaggg | aaaaggccgt | ggctataata | gaaaattgtg | ttcatcctga | ttacaaggat | 1500 |
| atgcttatgg | aatattttga | agaggcttgt | aagtcatcag | gtggaaatac | accacataat | 1560 |
| cttgaaaaag | ctcttttcctg | gcatacaaaa | tttataaaaa | ctggtagtat | gaaataa | 1617 |

<210> SEQ ID NO 2
<211> LENGTH: 1419
<212> TYPE: DNA
<213> ORGANISM: Unknown
<220> FEATURE:
<223> OTHER INFORMATION: SucD-coding gene

<400> SEQUENCE: 2

| | | | | | |
|---|---|---|---|---|---|
| atgagtaatg | aagtatctat | aaagaattta | attgaaaagg | caaaggcggc | acaaaaaaaa | 60 |
| ttggaagcct | atagtcaaga | acaagttgat | gtactagtaa | aagcactagg | aaaagtggtt | 120 |

| | |
|---|---|
| tatgataatg cagaaatgtt tgcaaaagaa gcagttgaag aaacagaaat gggtgtttat | 180 |
| gaagataaag tagctaaatg tcatttgaaa tcaggagcta tttggaatca tataaaagac | 240 |
| aagaaactg taggcataat aaaagaagaa cctgaaaggg cacttgttta tgttgctaag | 300 |
| ccaaagggag ttgtggcagc tactacgcct ataactaatc cagtggtaac tcctatgtgt | 360 |
| aatgcaatgg ctgctataaa gggcagaaat acaataatag tagcaccaca tcctaaagca | 420 |
| aagaaagttt cagctcatac tgtagaactt atgaatgctg agcttaaaaa attgggagca | 480 |
| ccagaaaata tcatacagat agtagaagca ccatcaagag aagctgctaa ggaacttatg | 540 |
| gaaagtgctg atgtagttat tgctacaggc ggtgctggaa gagttaaagc tgcttactcc | 600 |
| agtggaagac cagcttatgg cgttggacct ggaaattcac aggtaatagt tgataaggga | 660 |
| tacgattata acaaagctgc acaggatata ataacaggaa gaaaatatga caatggaatt | 720 |
| atatgttctt cagagcaatc agttatagct cctgctgaag attatgataa ggtaatagca | 780 |
| gcttttgtag aaaatgggc attctatgta gaagatgagg aaacagtaga aaagttttaga | 840 |
| tcaactttat ttaaagatgg aaaaataaac agcaagatta taggtaaatc cgtccaaatt | 900 |
| attgcggatc ttgcaggagt aaaagtacca gaaggtacta aggttatagt acttaagggt | 960 |
| aaaggtgcag gagaaaaaga tgtactttgt aaagaaaaaa tgtgtccagt tttagtagca | 1020 |
| ttgaaatatg atactttga agaagcagtt gaaatagcta tggctaatta tatgtatgaa | 1080 |
| ggagctggtc atacagcagg catacattct gacaatgacg agaacataag atatgcaaga | 1140 |
| actgtattac ctataagcag attagttgta aatcagcctg caactactgc tggaggaact | 1200 |
| gtattaccta taagcagatt agttgtaaat cagcctgcaa ctactgctgg aggaagtttc | 1260 |
| aataatggat ttaaccctac tactacacta ggctgcggat catggggcag aaacagtatt | 1320 |
| tcagaaaatc ttacttacga gcatcttata aatgtttcaa gatagggta tttcaataaa | 1380 |
| gaagcaaaag ttcctagcta tgaggaaata tggggataa | 1419 |

<210> SEQ ID NO 3
<211> LENGTH: 1116
<212> TYPE: DNA
<213> ORGANISM: Unknown
<220> FEATURE:
<223> OTHER INFORMATION: 4hbD-coding gene

<400> SEQUENCE: 3

| | |
|---|---|
| atgaagttat taaaattggc acctgatgtt tataaatttg atactgcaga ggagtttatg | 60 |
| aaatacttta aggttggaaa aggtgacttt atacttacta tgaattttt atataaacct | 120 |
| ttccttgaga aattcaatga tggtgcagat gctgtatttc aggagaaata tggactcggt | 180 |
| gaaccttctg atgaaatgat aaacaatata ttaaggata ttggagataa acaatataat | 240 |
| agaattattg ctgtaggggg aggatctgta atagatatag ccaaaatcct cagtcttaag | 300 |
| tatactgatg attcattgga tttgtttgag ggaaaagtac tcttgtaaa aacaaagaa | 360 |
| ttaattatag ttccaactac atgtggaaca ggttcagaag ttacaaatgt atcagttgca | 420 |
| gaattaaaga gaagacatac taaaaaagga attgcttcag acgaattata tgcaacttat | 480 |
| gcagtacttg taccagaatt tataaaagga cttccatata agtttttgt aaccagctcc | 540 |
| gtagatgcct aatacatgc aacagaagct tatgtatctc caaatgcaaa tccttatact | 600 |
| gatatgttta gtgtaaaagc tatggagtta attttaaatg atacatgca aatggtagag | 660 |
| aaaggaaatg attacagagt tgaaataatt gaggattttg ttataggcag caattatgca | 720 |
| ggtatagctt ttggaaatgc aggagtggga gcggttcacg cactctcata tccaataggc | 780 |

```
ggaaattatc atgtgcctca tggagaagca aattatctgt tttttacaga aatatttaaa      840
acttattatg agaaaaatcc aaatggcaag attaaagatg taaataaact attagcaggc      900
atactaaaat gtgatgaaag tgaagcttat gacagtttat cacaactttt agataaatta      960
ttgtcaagaa aaccattaag agaatatgga atgaaagagg aagaaattga aacttttgct     1020
gattcagtaa tagaaggaca gcagagactg ttggtaaaca attatgaacc ttttttcaaga    1080 gaagacatag taaacacata taaaaagtta tattaa                                1116

<210> SEQ ID NO 4
<211> LENGTH: 1460
<212> TYPE: DNA
<213> ORGANISM: Unknown
<220> FEATURE:
<223> OTHER INFORMATION: GHB-coding gene

<400> SEQUENCE: 4
gaattgtgaa cgatcgctcg attttagtat gatgccagat gttccaggtg cccggcagta      60
cgagataacc ccgaaaagtc gctgtcagcc tgccacgcgg caagttttttg cgcgatgatc    120 ggctgaagcg gtcccgaggg ctccggaaac gcagtagtgc aggtccattg aaacccaaga    180
cagcgggcct ggcgagcatc cgctccaggc ccgtgcaaaa dacaatttgg cggcagatcc    240
cggcaggaga caagcaaaca tggcgtttat ctactatctg acccacatcc acctggattt    300
cggcgcggta agcctgctca agtccgaatg cgagcgcatc ggcatccgcc gcccgttgct    360
ggtgaccgac aagggcgtgg tcgccgcggg agtggcgcag cgtgccatcg atgcaatgca    420
gggcctgcag gttgcggtat tcgatgaaac cccgtcgaac ccgaccgagg ccatggtgcg    480
caaggccgcc gcacaatacc gcgaggccgg ctgcgacggg ctggtggcag tgggcggcgg    540
ctcgtcgatc gacctcgcca agggcatcgc catcctggcc acgcatgagg gcgagctgac    600
cacctatgcc accatcgaag gcggcagcgc caggatcacc gacaaggcgg cgccgctgat    660
cgcggtgccc accacctcgg gcaccggcag cgaggtggcg cgcggcgcca tcatcatcct    720
ggacgacggc cgcaagctgg gcttccattc ctggcatttg ctgcccaagt ccgccgtctg    780
cgacccggaa ctgacgctgg ggctgccggc cgggctgacc gcggccaccg gcatggatgc    840
gatcgcgcac tgcatcgaga ccttcctggc ccccgccttc aacccgcccg cggacggcat    900
tgcgctggac gggctggagc gcggctgggg ccatatcgaa cgcgccaccc gcgacggtca    960
ggaccgcgac gcacgcctga acatgatgag cgcgtcgatg cagggcgcaa tggcgttcca   1020
gaaggggctg gctgcgtgc attcgctgtc gcaccgctg gcggggctga agatcgacgg    1080
ccgcaccggc ctgcaccacg gcacgctcaa cgcggtggtg atgccggcgg tgctgcgctt   1140
caacgccgat gcgcccacgg tggtgcgcga cgaccgctac gcacgcctgc gccgcgccat   1200
gcacctgccc gacggcgccg atatcgcgca ggccgtgcac gacatgaccg tgcgcctggg   1260
cctgcccacc gggctgcgtc agatgggtgt caccgaggac atgttcgaca aggtgattgc   1320
cggtgcgctg gtcgaccatt gccacaagac caacccgaaa gaagccagcg ccgcggatta   1380
tcggcgtatg cttgagcagt ccatgtagca cacagcggct tcccgccggt cagaccgacc   1440
aagcggctgt ccggcggccc                                               1460

<210> SEQ ID NO 5
<211> LENGTH: 1290
<212> TYPE: DNA
<213> ORGANISM: Unknown
<220> FEATURE:
<223> OTHER INFORMATION: 4HB-CoA transferase-coding gene
```

<400> SEQUENCE: 5

```
atggagtggg aagagatata taaagagaaa ctggtaactg cagaaaaagc tgtttcaaaa      60
atagaaaacc atagcagggt agttttttgca catgcagtag agaacccgt agatttagta    120
aatgcactag ttaaaaataa ggataattat ataggactag aaatagttca catggtagct    180
atgggcaaag gtgtatatac aaaagagggt atgcaaagac attttagaca taatgctttg    240
tttgtaggcg gatctactag agatgcagta aattcaggaa gagcagttta tacaccttgt    300
tttttctatg aagtgccaag tttgtttaaa gaaaacgtt tgcctgtaga tgtagcactt     360
attcaggtaa gtgagccaga taaatatggc tactgcagtt ttggagtttc caatgactat    420
accaagccag cagcagaaag tgctaagctt gtaattgcag aagtgaataa aaacatgcca    480
agaactcttg gagattcttt tatacatgta tcagatattg attatatagt ggaagcttca    540
cacccattgt tagaattgca gcctcctaaa ttgggagatg tagaaaaagc cataggagaa    600
aactgtgcat ctttaattga agatggagct actcttcagc ttggaatagg tgctatacca    660
gatgcggtac tttattcttt aaagaacaaa aagaatttag gaatacattc tgagatgata    720
tcagatggtg tgatggaact ggtgaaggca ggggttatca ataacaagaa aaagaccctc    780
catccaggca aaatagttgt aacattttta atgggaacaa aaaaattata tgattttgta    840
aacaataatc caatggtaga aacttattct gtagattatg taaataatcc actggtaatt    900
atgaaaaatg acaatatggt ttcaataaat tcttgtgttc aagtagactt aatgggacaa    960
gtatgttctg aaagtatagg attgaaacag ataagtggag tgggaggcca ggtagatttt   1020
attagaggag ctaatctatc aaagggtgga aaggctatta tagctatacc ttccacagct   1080
ggaaaaggaa agtttcaag aataactcca cttctagata ctggtgctgc agttacaact   1140
tctagaaatg aagtagatta tgtagttact gaatatggtg ttgctcatct taagggcaaa   1200
acttttaagaa ataggcaag agctctaata aatatcgctc atccaaaatt cagagaatca   1260
ttaatgaatg aatttaaaaa gagattttag                                    1290
```

<210> SEQ ID NO 6
<211> LENGTH: 906
<212> TYPE: DNA
<213> ORGANISM: Unknown
<220> FEATURE:
<223> OTHER INFORMATION: Ptb-coding gene

<400> SEQUENCE: 6

```
gtgattaaga gttttaatga aattatcatg aaggtaaaga gcaaagaaat gaaaaaagtt      60
gctgttgctg tagcacaaga cgagccagta cttgaagcag taagagatgc taagaaaaat    120
ggtattgcag atgctattct tgttggagac catgacgaaa tcgtgtcaat cgcgcttaaa    180
ataggaatgg atgtaaatga ttttgaaata gtaaacgagc ctaacgttaa gaaagctgct    240
ttaaaggcag tagagcttgt atcaactgga aaagctgata tggtaatgaa gggacttgta    300
aatacagcaa ctttcttaag atctgtatta acaaagaag ttggacttag aacaggaaaa    360
actatgtctc acgttgcagt atttgaaact gagaaatttg atagactatt attttttaaca    420
gatgttgctt tcaatactta tcctgaatta aggaaaaaa ttgatatagt aaacaattca    480
gttaaggttg cacatgcaat aggaattgaa atccaaagg ttgctccaat ttgtgcagtt    540
gaggttataa acctaaaat gccatcaaca cttgatgcag caatgctttc aaaaatgagt    600
gacagaggac aaattaaagg ttgtgtagtt gacggacctt tagcacttga tatagcttta    660
tcagaagaag cagcacatca taagggagta acaggagaag ttgctggaaa agctgatatc    720
```

| ttcttaatgc caaacataga acaggaaat gtaatgtata agactttaac atatacaact | 780 |
| gattcaaaaa atggaggaat cttagttgga acttctgcac cagttgtttt aacttcaaga | 840 |
| gctgacagcc atgaaacaaa atgaactct atagcacttg cagctttagt tgcaggcaat | 900 |
| aaataa | 906 |

<210> SEQ ID NO 7
<211> LENGTH: 1068
<212> TYPE: DNA
<213> ORGANISM: Unknown
<220> FEATURE:
<223> OTHER INFORMATION: Buk-coding gene

<400> SEQUENCE: 7

| atgtatagat tactaataat caatcctggc tcgacctcaa ctaaaattgg tatttatgac | 60 |
| gatgaaaaag agatatttga aagacttta agacattcag ctgaagagat agaaaaatat | 120 |
| aacactatat ttgatcaatt tcaattcaga aagaatgtaa ttttagatgc gttaaaagaa | 180 |
| gcaaacatag aagtaagttc tttaaatgct gtagttggaa gaggcggact cttaaagcca | 240 |
| atagtaagtg gaacttatgc agtaaatcaa aaaatgcttg aagaccttaa agtaggagtt | 300 |
| caaggtcagc atgcgtcaaa tcttggtgga attattgcaa atgaaatagc aaaagaaata | 360 |
| aatgttccag catacatagt tgatccagtt gttgtggatg agcttgatga agtttcaaga | 420 |
| atatcaggaa tggctgacat tccaagaaaa agtatattcc atgcattaaa tcaaaaagca | 480 |
| gttgctagaa gatatgcaaa agaagttgga aaaaaatacg aagatcttaa tttaatcgta | 540 |
| gtccacatgg gtggaggtac ttcagtaggt actcataaag atggtagagt aatagaagtt | 600 |
| aataatacac ttgatggaga aggtccattc tcaccagaaa gaagtggtgg agttccaata | 660 |
| ggagatcttg taagattgtg cttcagcaac aaatatactt atgaagaagt aatgaaaaag | 720 |
| ataaacggca aggcggagt tgttagttac ttaaatacta tcgattttaa ggctgtagtt | 780 |
| gataaagctc ttgaaggaga taagaaatgt gcacttatat atgaagcttt cacattccag | 840 |
| gtagcaaaag agataggaaa atgttcaacc gttttaaaag gaaatgtaga tgcaataatc | 900 |
| ttaacaggcg gaattgcgta caacgagcat gtatgtaatg ccatagagga tagagtaaaa | 960 |
| ttcatagcac ctgtagttag atatggtgga gaagatgaac ttcttgcact tgcagaaggt | 1020 |
| ggacttagag ttttaagagg agaagaaaaa gctaaggaat acaaataa | 1068 |

<210> SEQ ID NO 8
<211> LENGTH: 2577
<212> TYPE: DNA
<213> ORGANISM: Unknown
<220> FEATURE:
<223> OTHER INFORMATION: Butyl-CoA dehydrogenase(CAP0035)-coding gene

<400> SEQUENCE: 8

| atgaaagtta caaatcaaaa agaactaaaa caaaagctaa atgaattgag agaagcgcaa | 60 |
| aagaagtttg caacctatac tcaagagcaa gttgataaaa ttttttaaaca atgtgccata | 120 |
| gccgcagcta agaaagaat aaacttagct aaattagcag tagaagaaac aggaataggt | 180 |
| cttgtagaag ataaaattat aaaaaatcat tttgcagcag aatatatata caataaatat | 240 |
| aaaaatgaaa aaacttgtgg cataatagac catgacgatt ctttaggcat aacaaaggtt | 300 |
| gctgaaccaa ttggaattgt tgcagccata gttcctacta ctaatccaac ttccacagca | 360 |
| atttcaaat cattaatttc tttaaaaaca agaaacgcaa tattcttttc accacatcca | 420 |
| cgtgcaaaaa aatctacaat tgctgcagca aaattaattt tagatgcagc tgttaaagca | 480 |

```
ggagcaccta aaaatataat aggctggata gatgagccat caatagaact ttctcaagat    540
ttgatgagtg aagctgatat aatattagca acaggaggtc cttcaatggt taaagcggcc    600
tattcatctg gaaaacctgc aattggtgtt ggagcaggaa atacaccagc aataatagat    660
gagagtgcag atatagatat ggcagtaagc tccataattt tatcaaagac ttatgacaat    720
ggagtaatat gcgcttctga acaatcaata ttagttatga attcaatata cgaaaaagtt    780
aaagaggaat ttgtaaaacg aggatcatat atactcaatc aaaatgaaat agctaaaata    840
aaagaaacta tgtttaaaaa tggagctatt aatgctgaca tagttggaaa atctgcttat    900
ataattgcta aaatggcagg aattgaagtt cctcaaacta caaagatact tataggcgaa    960
gtacaatctg ttgaaaaaag cgagctgttc tcacatgaaa aactatcacc agtacttgca   1020
atgtataaag ttaaggattt tgatgaagct ctaaaaaagg cacaaaggct aatagaatta   1080
ggtggaagtg acacacgtc atctttatat atagattcac aaaacaataa ggataaagtt   1140
aaagaatttg gattagcaat gaaaacttca aggacattta ttaacatgcc ttcttcacag   1200
ggagcaagcg gagatttata caattttgcg atagcaccat catttactct tggatgcggc   1260
acttggggag gaaactctgt atcgcaaaat gtagagccta acatttatt aaatattaaa   1320 agtgttgctg aaagaaggga aaatatgctt tggtttaaag tgccacaaaa aatatatttt   1380
aaatatggat gtcttagatt tgcattaaaa gaattaaaag atatgaataa gaaaagagcc   1440
tttatagtaa cagataaaga tcttttttaaa cttggatatg ttaataaaat aacaaaggta   1500
ctagatgaga tagatattaa atacagtata tttacagata ttaaatctga tccaactatt   1560
gattcagtaa aaaaaggtgc taagaaatg cttaactttg aacctgatac tataatctct   1620
attggtggtg gatcgccaat ggatgcagca aaggttatgc acttgttata tgaatatcca   1680
gaagcagaaa ttgaaaatct agctataaac tttatggata taagaaagag aatatgcaat   1740
ttccctaaat taggtacaaa ggcgatttca gtagctattc ctacaactgc tggtaccggt   1800
tcagaggcaa cacctttgc agttataact aatgatgaaa caggaatgaa atacccttta   1860
acttcttatg aattgacccc aaacatggca ataatagata ctgaattaat gttaaatatg   1920
cctagaaaat taacagcagc aactggaata gatgcattag ttcatgctat agaagcatat   1980
gtttcggtta tggctacgga ttatactgat gaattagcct taagagcaat aaaaatgata   2040
tttaaatatt tgcctagagc ctataaaaat gggactaacg acattgaagc aagagaaaaa   2100
atggcacatg cctctaatat tgcggggatg gcatttgcaa atgctttctt aggtgtatgc   2160
cattcaatgg ctcataaact tggggcaatg catcacgttc acatggaat tgcttgtgct   2220 gtattaatag aagaagttat taaatataac gctacagact gtccaacaaa gcaaacagca   2280
ttccctcaat ataaatctcc taatgctaag agaaaatatg ctgaaattgc agagtatttg   2340
aatttaaagg gtactagcga taccgaaaag gtaacagcct aatagaagc tatttcaaag   2400 ttaaagatag atttgagtat tccacaaaat ataagtgccg ctggaataaa taaaaaagat   2460
ttttataata cgctagataa aatgtcagag cttgcttttg atgaccaatg tacaacagct   2520
aatcctaggt atccacttat aagtgaactt aaggatatct atataaaatc attttaa      2577
```

<210> SEQ ID NO 9
<211> LENGTH: 2589
<212> TYPE: DNA
<213> ORGANISM: Unknown
<220> FEATURE:
<223> OTHER INFORMATION: Butyl-CoA dehydrogenase(CAP0162)-coding gene

<400> SEQUENCE: 9

```
atgaaagtca caacagtaaa ggaattagat gaaaaactca aggtaattaa agaagctcaa      60
aaaaaattct cttgttactc gcaagaaatg gttgatgaaa tctttagaaa tgcagcaatg     120
gcagcaatcg acgcaaggat agagctagca aaagcagctg ttttggaaac cggtatgggc     180
ttagttgaag acaaggttat aaaaaatcat tttgcaggcg aatacatcta taacaaatat     240
aaggatgaaa aaacctgcgg tataattgaa cgaaatgaac cctacggaat tacaaaaata     300
gcagaaccta taggagttgt agctgctata atccctgtaa caaaccccac atcaacaaca     360
atatttaaat ccttaatatc ccttaaaact agaaatggaa ttttcttttc gcctcaccca     420
agggcaaaaa aatccacaat actagcagct aaaacaatac ttgatgcagc cgttaagagt     480
ggtgccccgg aaaatataat aggttggata gatgaaccct caattgaact aactcaatat     540
ttaatgcaaa aagcagatat aaccctttgca actggtggtc cctcactagt taaatctgct     600
tattcttccg aaaaccagc aataggtgtt ggtccgggta acaccccagt aataattgat     660
gaatctgctc atataaaaat ggcagtaagt tcaattatat atccaaaac ctatgataat      720
ggtgttatat gtgcttctga acaatctgta atagtcttaa aatccatata taacaaggta     780
aaagatgagt tccaagaaag aggagcttat ataataaaga aaacgaatt ggataaagtc      840
cgtgaagtga tttttaaaga tggatccgta aaccctaaaa tagtcggaca gtcagcttat     900
actatagcag ctatggctgg cataaaaagta cctaaaacca aagaatatt aataggagaa      960
gttacctcct taggtgaaga agaaccttt gcccacgaaa actatctcc tgtttttggct     1020
atgtatgagg ctgacaattt tgatgatgct ttaaaaaaag cagtaactct aataaactta     1080
ggaggcctcg gccataccctc aggaatatat gcagatgaaa taaaagcacg agataaaata     1140
gatagattta gtgagccat gaaaaccgta agaacctttg taaatatccc aacctcacaa     1200
ggtgcaagtg gagatctata taattttaga ataccaccctt cttcacgct tggctgcgga     1260
ttttggggag gaaattctgt ttccgagaat gttggtccaa acatctttt gaatattaaa     1320
accgtagctg aaaggagaga aaacatgctt tggtttagag ttccacataa agtatatttt     1380
aagttcggtt gtcttcaatt tgcttttaaaa gatttaaaag atctaaagaa aaaaagagcc     1440
tttatagtta ctgatagtga cccctataat ttaaactatg ttgattcaat aataaaaata     1500
cttgagcacc tagatattga tttttaaagta tttaataagg ttggaagaga agctgatctt     1560
aaaaccataa aaaaagcaac tgaagaaatg tcctccttta tgccagacac tataatagct     1620
ttaggtggta cccctgaaat gagctctgca aagctaatgt gggtactata tgaacatcca     1680
gaagtaaaat ttgaagatct tgcaataaaaa tttatggaca taagaaagag aatatatact     1740
ttcccaaaac tcggtaaaaa ggctatgtta gttgcaatta caacttctgc tggttccggt     1800
tctgaggtta ctccttttgc tttagtaact gacaataaca ctggaaataa gtacatgtta     1860
gcagattatg aaatgacacc aaatatggca attgtagatg cagaacttat gatgaaaatg     1920
ccaaagggat taaccgctta ttcaggtata gatgcactag taaatagtat agaagcatac     1980
acatccgtat atgcttcaga atacacaaac ggactagcac tagaggcaat acgattaata     2040
tttaaatatt tgcctgaggc ttacaaaaac ggaagaacca atgaaaaagc aagagagaaa     2100
atggctcacg cttcaactat ggcaggtatg gcatccgcta atgcatttct aggtctatgt     2160
cattccatgg caataaaatt aagttcagaa cacaatattc ctagtggcat tgccaatgca     2220
ttactaatag aagaagtaat aaaatttaac gcagttgata atcctgtaaa acaagcccct     2280
tgcccacaat ataagtatcc aaacaccata tttagatatg ctcgaattgc agattatata     2340
```

```
aagcttggag gaaatactga tgaggaaaag gtagatctct taattaacaa atacatgaa    2400 ctaaaaaaag ctttaaatat accaacttca ataaggatg caggtgtttt ggaggaaaac    2460
ttctattcct cccttgatag aatatctgaa cttgcactag atgatcaatg cacaggcgct    2520
aatcctagat ttcctcttac aagtgagata aagaaatgt atataaattg ttttaaaaaa    2580
caaccttaa                                                           2589
```

<210> SEQ ID NO 10
<211> LENGTH: 1449
<212> TYPE: DNA
<213> ORGANISM: Unknown
<220> FEATURE:
<223> OTHER INFORMATION: GabD-coding gene

<400> SEQUENCE: 10

```
atgaaactta acgacagtaa cttattccgc cagcaggcgt tgattaacgg ggaatggctg      60
gacgccaaca atggtgaagc catcgacgtc accaatccgg cgaacggcga caagctgggt     120
agcgtgccga aaatgggcgc ggatgaaacc cgcgccgcta tcgacgccgc caaccgcgcc     180
ctgcccgcct ggcgcgcgct caccgccaaa gaacgcgcca ccattctgcg caactggttc     240
aatttgatga tggagcatca ggacgattta gcgcgcctga tgaccctcga acagggtaaa     300
ccactggccg aagcgaaagg cgaaatcagc tacgccgcct cctttattga gtggtttgcc     360
gaagaaggca aacgcattta tggcgacacc attcctggtc atcaggccga taacgcctg      420 attgttatca agcagccgat tggcgtcacc gcggctatca cgccgtggaa cttcccggcg     480
gcgatgatta cccgcaaagc cggtccggcg ctggcagcag gctgcaccat ggtgctgaag     540
cccgccagtc agacgccgtt ctctgcgctg gcgctggcgg agctggcgat ccgcgcgggc     600
gttccggctg gggtatttaa cgtggtcacc ggttcggcgg gcgcggtcgg taacgaactg     660
accagtaacc cgctggtgcg caaactgtcg tttaccggtt cgaccgaaat tggccgccag     720
ttaatggaac agtgcgcgaa agacatcaag aaagtgtcgc tggagctggg cggtaacgcg     780
ccgtttatcg tctttgacga tgccgacctc gacaaagccg tggaaggcgc gctggcctcg     840
aaattccgca acgccgggca aacctgcgtc tgcgccaacc gcctgtatgt gcaggacggc     900
gtgtatgacc gttttgccga aaattgcag caggcagtga gcaaactgca catcggcgac     960
gggctggata acgcgtcac catcgggccg ctgatcgatg aaaaagcggt agcaaaagtg    1020
gaagagcata ttgccgatgc gctggagaaa ggcgcgcgcg tggtttgcgg cggtaaagcg    1080
cacgaacgcg cggcaacttc cttccagccg accattctgg tggacgttcc ggccaacgcc    1140
aaagtgtcga agaagagac gttcggcccc ctcgccccgc tgttccgctt taaagatgaa    1200
gctgatgtga ttgcgcaagc caatgacacc gagtttggcc ttgccgccta tttctacgcc    1260
cgtgatttaa gccgcgtctt ccgcgtgggc gaagcgctgg agtacggcat cgtcggcatc    1320
aataccggca ttatttccaa tgaagtggcc ccgttcggcg gcatcaaagc ctcgggtctg    1380
ggtcgtgaag gttcgaagta tggcatcgaa gattacttag aaatcaaata tatgtgcatc    1440
ggtctttaa                                                            1449
```

<210> SEQ ID NO 11
<211> LENGTH: 1287
<212> TYPE: DNA
<213> ORGANISM: Unknown
<220> FEATURE:
<223> OTHER INFORMATION: DctA-coding gene

<400> SEQUENCE: 11

```
atgaaaacct ctctgtttaa aagcctttac tttcaggtcc tgacagcgat agccattggt    60
attctccttg gccatttcta tcctgaaata ggcgagcaaa tgaaaccgct tggcgacggc   120
ttcgttaagc tcattaagat gatcatcgct cctgtcatct tttgtaccgt cgtaacgggc   180
attgcgggca tggaaagcat gaaggcggtc ggtcgtaccg gcgcagtcgc actgctttac   240
tttgaaattg tcagtaccat cgcgctgatt attggtctta tcatcgttaa cgtcgtgcag   300
cctggtgccg aatgaacgt cgatccggca acgcttgatg cgaaagcggt agcggtttac    360
gccgatcagg cgaaagacca gggcattgtc gccttcatta tggatgtcat cccggcgagc   420
gtcattggcg catttgccag cggtaacatt ctgcaggtgc tgctgtttgc cgtactgttt   480
ggttttgcgc tccaccgtct gggcagcaaa ggccaactga tttttaacgt catcgaaagt   540
ttctcgcagg tcatcttcgg catcatcaat atgatcatgc gtctggcacc tattggtgcg   600
ttcggggcaa tggcgtttac catcggtaaa tacggcgtcg gcacactggt gcaactgggg   660
cagctgatta tctgtttcta cattacctgt atcctgtttg tggtgctggt attgggttca   720
atcgctaaag cgactggttt cagtatcttc aaatttatcc gctacatccg tgaagaactg   780
ctgattgtac tggggacttc atcttccgag tcggcgctgc cgcgtatgct cgacaagatg   840
gagaaactcg gctgccgtaa atcggtggtg gggctggtca tcccgacagg ctactcgttt   900
aaccttgatg gcacatcgat atacctgaca atggcggcgg tgtttatcgc ccaggccact   960
aacagtcaga tggatatcgt ccaccaaatc acgctgttaa tcgtgttgct gctttcttct  1020
aaaggggcgg caggggtaac gggtagtggc tttatcgtgc tggcggcgac gctctctgcg  1080
gtgggccatt tgccggtagc gggtctggcg ctgatcctcg gtatcgaccg ctttatgtca  1140
gaagctcgtg cgctgactaa cctggtcggt aacggcgtag cgaccattgt cgttgctaag  1200
tgggtgaaag aactggacca caaaaaactg gacgatgtgc tgaataatcg tgcgccggat  1260
ggcaaaacgc acgaattatc ctcttaa                                      1287
```

<210> SEQ ID NO 12
<211> LENGTH: 44
<212> TYPE: DNA
<213> ORGANISM: Artificial Sequence
<220> FEATURE:
<223> OTHER INFORMATION: Cat1f-SacI primer

<400> SEQUENCE: 12

```
tttcccgagc tctgtgaggc gattaaatga gtaaagggat aaag                     44
```

<210> SEQ ID NO 13
<211> LENGTH: 40
<212> TYPE: DNA
<213> ORGANISM: Artificial Sequence
<220> FEATURE:
<223> OTHER INFORMATION: 4hbDb-XabI primer

<400> SEQUENCE: 13

```
gctctagatt agataaaaaa gaggacattt cacaatatgg                          40
```

<210> SEQ ID NO 14
<211> LENGTH: 31
<212> TYPE: DNA
<213> ORGANISM: Artificial Sequence
<220> FEATURE:
<223> OTHER INFORMATION: DctAf-EcoRI primer -continued

<400> SEQUENCE: 14
ggaattcatg aaaacctctc tgtttaaaag c           31

<210> SEQ ID NO 15
<211> LENGTH: 35
<212> TYPE: DNA
<213> ORGANISM: Artificial Sequence
<220> FEATURE:
<223> OTHER INFORMATION: DctAb-XbaI primer

<400> SEQUENCE: 15
gctctagatt aagaggataa ttcgtgcgtt ttgcc       35

<210> SEQ ID NO 16
<211> LENGTH: 33
<212> TYPE: DNA
<213> ORGANISM: Artificial Sequence
<220> FEATURE:
<223> OTHER INFORMATION: CAP0035f-SacI primer

<400> SEQUENCE: 16
tttcccgagc tcatgaaagt tacaaatcaa aaa         33

<210> SEQ ID NO 17
<211> LENGTH: 29
<212> TYPE: DNA
<213> ORGANISM: Artificial Sequence
<220> FEATURE:
<223> OTHER INFORMATION: CAP0035b-XbaI primer

<400> SEQUENCE: 17
gctctagatt aaaatgcttt tatatagat              29

<210> SEQ ID NO 18
<211> LENGTH: 28
<212> TYPE: DNA
<213> ORGANISM: Artificial Sequence
<220> FEATURE:
<223> OTHER INFORMATION: CAP0162f-EcoRI primer

<400> SEQUENCE: 18
ggaattcatg aaagtcacaa cagtaaag               28

<210> SEQ ID NO 19
<211> LENGTH: 26
<212> TYPE: DNA
<213> ORGANISM: Artificial Sequence
<220> FEATURE:
<223> OTHER INFORMATION: CAP0162b-XbaI primer

<400> SEQUENCE: 19
gctctagatt aaggttgttt tttaaa                 26

<210> SEQ ID NO 20
<211> LENGTH: 34
<212> TYPE: DNA
<213> ORGANISM: Artificial Sequence
<220> FEATURE:
<223> OTHER INFORMATION: cat2f-EcoRI primer

<400> SEQUENCE: 20
ggaattcatg gagtgggaag agatatataa agag        34

```
<210> SEQ ID NO 21
<211> LENGTH: 40
<212> TYPE: DNA
<213> ORGANISM: Artificial Sequence
<220> FEATURE:
<223> OTHER INFORMATION: cat2b-BamHI primer

<400> SEQUENCE: 21
cgggatcctt aaaatctctt tttaaattca ttcattaatg                    40

<210> SEQ ID NO 22
<211> LENGTH: 37
<212> TYPE: DNA
<213> ORGANISM: Artificial Sequence
<220> FEATURE:
<223> OTHER INFORMATION: ptbf-EcoRI primer

<400> SEQUENCE: 22
ggaattcatg attaagagtt ttaatgaaat tatcatg                       37

<210> SEQ ID NO 23
<211> LENGTH: 38
<212> TYPE: DNA
<213> ORGANISM: Artificial Sequence
<220> FEATURE:
<223> OTHER INFORMATION: bukb-XbaI primer

<400> SEQUENCE: 23
gctctagatt atttgtattc cttagctttt tcttctcc                      38
```

MUTANTS HAVING CAPABILITY TO PRODUCE 1, 4-BUTANEDIOL AND METHOD FOR PREPARING 1, 4-BUTANEDIOL USING THE SAME

This application claims the benefit of PCT/KR2008/004700 filed on Aug. 13, 2008 and Korean Patent Application No. 10-2007-0091081 filed on Sep. 7, 2007, all of which are hereby incorporated herein by reference for all purposes in their entirety.

TECHNICAL FIELD

The present invention relates to a mutant microorganism capable of producing 1,4-butanediol and a method of preparing 1,4-butanediol using the same.

BACKGROUND ART

Biodegradable polymers have been suggested as an alternative to synthetic polymers, which are one of the major causes of serious environmental pollution. Among various biodegradable polymers currently being developed, poly-β-hydroxybutyrate, a biodegradable polymer stored by various microorganisms in a state of unbalanced nutrition, has excellent characteristics such as biodegradability, water-resistance, piezoelectricity and biocompatibility. In particular, 4-hydroxybutyrate, an example of polyhydroxyalkanoate (PHA), has polyester-like characteristics and exhibits a wide range of properties from those of crystalline plastic to highly elastic rubber. Therefore, a considerable amount of research into microbial biodegradable plastic is presently being conducted.

Further, 4-hydroxybutyrate can be easily converted into various chemicals having 4 carbon atoms, such as 1,4-butanediol, γ-butyrolactone (GBL) and THF. In particular, 1,4-butanediol is an important industrial chemical in various forms such as polymer, solvent and a fine chemical intermediate. Although most chemicals having 4 carbon atoms are currently synthesized from 1,4-butanediol, maleic anhydride and so on, increasing production costs caused by an increase in the price of oil is necessitating development of another process for compensating and substituting a conventional chemical production process. A biological process has been suggested as such an alternative.

Meanwhile, succinate, dicarboxylic acid having 4 carbon atoms, is a kind of organic acid produced when a microorganism is cultured in an anaerobic condition. Now, various microorganisms are used as succinate-producing cells, and its production cost has become lower due to an effective fermentation process and development of a separation and purification process. Also, 4-hydroxybutyrate may be produced from succinate, and various organic acids having 4 carbon atoms can be derived from 4-hydroxybutyrate.

PCT Publication No. WO 2005/052135 is an example of a patent application disclosing a method of efficiently producing succinate, in which a Lumen bacterial mutant produces succinate in high concentration without producing other organic acids, and a method of preparing succinate using the mutant. In addition, a method of preparing an E. coli mutant capable of producing succinate in high concentration is disclosed in Korean Patent Application No. 10-2004-60149, and a method of preparing succinate using a novel gene is disclosed in Korean Patent Application Nos. 10-2005-0076301, 10-2005-0076317 and 10-2005-0076348.

As explained above, there is strong demand for a mutant capable of producing 1,4-butanediol, an industrially important chemical having 4 carbon atoms, and a biological method of preparing 1,4-butanediol using the mutant.

DISCLOSURE

Technical Problem

The present invention is directed to providing a mutant microorganism capable of producing 1,4-butanediol with high efficiency and a method of preparing 1,4-butanediol using the same.

Technical Solution

In one aspect, a microorganism capable of producing succinate, and preferably, a mutant exhibiting high production of 1,4-butanediol, in which a gene encoding an enzyme converting succinate into 4-hydroxybutyrate and a gene encoding an enzyme converting 4-hydroxybutyrate into 1,4-butanediol are introduced or amplified, and a method of preparing 1,4-butanediol using the same, are provided.

In another aspect, a butyl-CoA dehydrogenase gene of SEQ ID NO: 8 or 9, which effectively produces 1,4-butanediol from 4-hydroxybutyl-CoA, and a recombinant vector having the same are provided.

Hereinafter, the present invention will be described in more detail.

As a result of efforts to prepare 1,4-butanediol using a microorganism capable of producing succinate, the present inventors developed a mutant microorganism producing 1,4-butanediol by inducing or amplifying a gene associated with 4-hydroxybutyrate biosynthesis and/or a gene associated with 1,4-butanediol biosynthesis in the microorganism capable of producing succinate, and found that the mutant microorganism effectively produced 1,4-butanediol. This finding led to the present invention.

The term "amplification" used herein means an increase in gene expression level compared to original expression level. If there is no gene to be amplified in a microorganism before mutation, the at least one gene may be introduced to the microorganism and then amplified. And if there is a gene to be amplified in a microorganism before mutation, the at least one gene may be introduced to the microorganism by the same method described above, or a gene originally present in the microorganism may be manipulated by a genetic engineering technique to increase gene expression. For example, when a gene amplifying expression is present in a microorganism to be mutated, an original promoter for operating gene expression may be substituted with a stronger promoter, thereby amplifying gene expression.

The microorganism capable of producing succinate may exhibit high production of succinate, the microorganism being preferably one selected from the group consisting of bacteria, yeast and fungi, and more particularly, bacteria, for example, Lumen bacteria, Corynebacterium species, Brevibacterium species and E. coli.

The Lumen bacteria may have inactive genes encoding lactate dehydrogenase (ldhA) and pyruvate-formate lyase (pfl), and produce succinate in high concentration without other organic acids under anaerobic conditions.

The term "inactivation" used herein means that a gene is not transcribed due to mutation, or transcribed mRNA is not properly translated into original protein. In order to deactivate a gene, mutation may be conducted by missing a gene or changing a nucleic acid sequence of a gene.

Further, the Lumen bacteria may have inactive genes encoding lactate dehydrogenase (ldhA), pyruvate-formate lyase (pfl), phosphotransacetylase (pta) and acetate kinase (ackA), and produce succinate in high concentration without substantial production of other organic acids in an anaerobic condition.

Alternatively, the Lumen bacteria may have inactive genes encoding lactate dehydrogenase (ldhA), pyruvate-formate lyase (pfl) and phosphopyruvate carboxylase (ppc), and produce succinate in high concentration without substantial production of other organic acids in an anaerobic condition.

The Lumen bacteria may be selected from the group consisting of *Mannheimia* sp., *Actinobacillus* sp. and *Anaerobiospirllum* sp., but the present invention is not limited to these examples. *Mannheimia* sp. is preferable, and *Mannheimia succiniciproducens* MBEL55E (KCTC 0769BP), *Mannheimia* sp. LPK (KCTC 10558BP), LPK4 and LPK7 (KCTC 10626BP) are more preferable.

The *E. coli* may have inactive genes encoding glucose phosphotransferase (ptsG) and pyruvate kinase (pykA and pykF), and produce succinate in high concentration without substantial production of other organic acids in an anaerobic condition. In particular, the *E. coli* mutant is preferably W3110GFA disclosed in Korean Patent Publication No. 10-2006-0011345.

Among the above-mentioned microorganisms producing succinate in high concentration, the Lumen bacteria may be prepared in a method disclosed in PCT Publication No. WO 2005/052135. That is, a gene of lactic dehydrogenase (ldhA) and a gene of pyruvate-formate lyase (pfl) are inactivated in *Mannheimia succiniciproducens* 55E, thereby constructing a mutant strain, i.e., *Mannheimia* sp. LPK (KCTC 10558BP). Then, in the LPK strains, genes of phosphotransacetylase gene (pta) and acetate kinase gene (ackA), and a gene of phosphopyruvate carboxylase (ppc), are independently inactivated, thereby constructing mutant strains (*Mannheimia* sp. LPK7 and LPK4) which are then cultured in an anaerobic condition to produce succinate with high yield.

In addition, among the microorganisms producing succinate in high concentration, *E. coli* may be constructed by a method disclosed in Korean Patent Publication No. 10-2006-0011345. That is, mutant *E. coli* strain W3110GFA is yielded by inactivating a gene encoding glucose phosphotransferase (ptsG) and two genes encoding pyruvate kinase (pykA and pykF) in W3110 strain transformed with a recombinant expression vector expressing a bacteriophage red operon (exo-beta-gam). Then, when the mutant *E. coli* strain W3110GFA is cultured in an anaerobic condition, it can be confirmed that productivity of the mutant is greater than that of a mother strain W3110.

A gene of an enzyme converting the succinate into 4-hydroxybutyrate and a gene of an enzyme associated with conversion of the succinate semialdehyde into succinate may be derived from *Clostridium kluyveri*, and a gene of an enzyme converting the 4-hydroxybutyrate into 1,4-butanediol may be derived from *Clostridium acetobutylicum*. Although *Clostridium kluyveri* and *Clostridium acetobutylicum* do not produce 4-hydroxybutyrate and 1,4-butanediol, the enzymes cloned in these strains play an important role in producing 4-hydroxybutyrate and 1,4-butanediol.

Further, the gene of the enzyme converting succinate into 4-hydroxybutyrate may be selected from the group consisting of a gene encoding succinyl-CoA transferase a gene encoding succinate semialdehyde dehydrogenase (SucD), a gene encoding 4-hydroxybutyrate dehydrogenase (hbD), and a gene encoding 4-hydroxybutyrate dehydrogenase (GHB). Preferably, the gene encoding Cat1 has a base sequence of SEQ ID NO: 1, the gene encoding SucD has a base sequence of SEQ ID NO: 2, the gene encoding 4hbD has a base sequence of SEQ ID NO: 3, and the gene encoding GHB has a base sequence of SEQ ID NO: 4.

For example, a mutant microorganism according to the present invention may have a gene encoding Cat1, a gene encoding SucD and a gene encoding 4hbD, or a gene encoding Cat1, a gene encoding SucD and a gene encoding GHB, but the present invention is not limited to these examples.

Further, effective use of succinate is very important to accomplish the object of the present invention, and thus succinic semialdehyde dehydrogenase (GabD) associated with conversion of succinic semialdehyde into succinate may be removed from recombinant *E. coli* of the microorganisms producing succinate in high concentration. Therefore, the mutant microorganism according to the present invention may also have an inactive gene associated with conversion of succinate semialdehyde into succinate, which is preferably a gene encoding succinic GabD. The gene encoding GabD has a base sequence of SEQ ID NO: 10, but the present invention is not limited to the sequence.

Also, to effectively transport succinate in a microorganism, C4-dicarboxylate transport protein (DctA) enzyme associated with transport of succinate may be amplified. Thus, the mutant microorganism may further have a gene encoding Dct4 associated with transport of succinate, which is introduced thereinto or amplified, and a gene encoding Dct4 preferably has a base sequence of SEQ ID NO: 11.

The genes of enzymes converting 4-hydroxybutyrate into 1,4-butanediol may be genes encoding 4-hydroxybutyrate-CoA transferase and alcohol dehydrogenase reducing 4-hydroxybutyrate-CoA, or genes encoding phosphotransbutyrylase, butyryl kinase and alcohol dehydrogenase reducing 4-hydroxybutyrate-CoA.

The gene encoding 4-hydroxybutyrate-CoA transferase may have a base sequence of SEQ ID NO: 5, which may be substituted with phosphotransbutyrylase (ptb; SEQ ID NO: 6) and butyryl kinase (BuK; SEQ ID NO: 7) to convert 4-hydroxybutyrate into 4-hydroxybutyrate-CoA.

The alcohol dehydrogenase may be butyl-CoA dehydrogenase derived from *Clostridium acetobutylicum*, and the gene encoding butyl-CoA dehydrogenase preferably has a base sequence of SEQ ID NO: 8 or 9 (CAP0035 or CAP0162). The genes of SEQ. ID. NOs: 8 and 9 are very useful to produce 1,4-butanediol in the mutant microorganism according to the present invention. Accordingly, the present invention provides a gene encoding butyl-CoA dehydrogenase and a recombinant vector containing the same.

The term "vector" means a DNA construct containing a DNA sequence operably linked to a control sequence suitable for expressing DNA in a suitable host. In the present invention, the vector may comprise a plasmid vector, a bacteriophage vector, a cosmid vector, a Yeast Artificial Chromosome (YAC) vector, and preferably a plasmid vector. For example, the plasmid vector may have a constitution comprising (a) a replication origin for effective replication to have several hundreds of copies in one host cell, (b) an antibiotic-resistance gene for selecting a host cell transformed with the plasmid vector, and (c) a restriction enzyme site into which a foreign DNA fragment is capable of being inserted. Although there is no suitable restriction enzyme site, the vector may be easily ligated with the foreign DNA using a synthetic oligonucleotide adaptor or a linker according to a conventional method.

Therefore, the present invention provides a microorganism capable of producing succinate, and preferably, a mutant microorganism exhibiting high production of 1,4-butanediol in which a gene encoding GabD is inactivated, and all of a gene encoding Cat1, a gene encoding SucD, a gene encoding 4hbD (or GHB), a gene encoding 4-hydroxybutyrate-CoA transferase and a gene encoding butyl-CoA dehydrogenase are introduced or amplified.

Further, the present invention provides a microorganism capable of producing succinate, and preferably, a mutant microorganism exhibiting high production of 1,4-butanediol in which a gene encoding 4-hydroxybutyrate-CoA transferase (or a gene encoding phosphobutyrylase and a gene encoding butyryl kinase) and a gene encoding butyl-CoA dehydrogenase are introduced or amplified, and a method of preparing 1,4-butanediol using the same.

The present invention further provides a method of preparing 1,4-butanediol comprising culturing the mutant in a medium containing a carbon source, and obtaining 1,4-butanediol from the culture.

Advantageous Effects

As described above in detail, the present invention provides a microorganism capable of producing succinate in high concentration, and more particularly, a mutant exhibiting high production of 1,4-butanediol that is a chemical having 4 carbon atoms having a wide range of important applications in chemical industry, and a biological method of preparing 1,4-butanediol using the same.

MODES OF THE INVENTION

Figure 1:
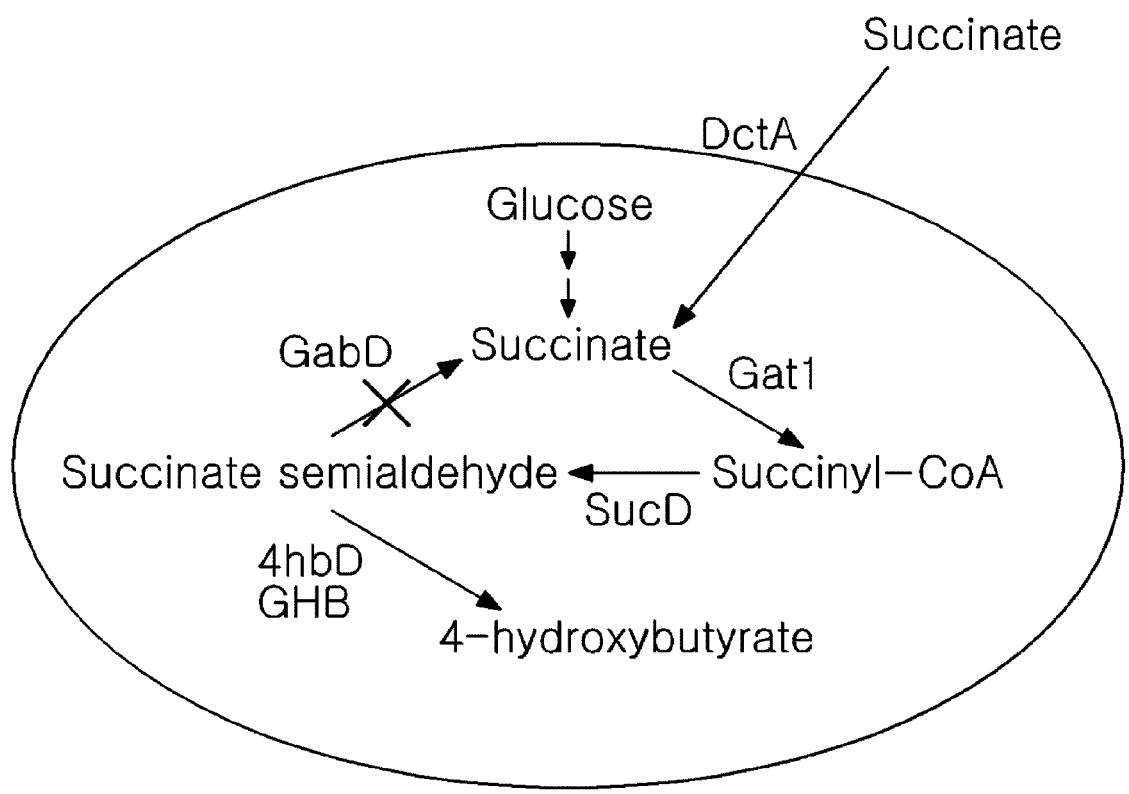
FIG. 1 is a schematic diagram of a pathway for producing 4-hydroxybutyrate from succinate.
Figure 2:
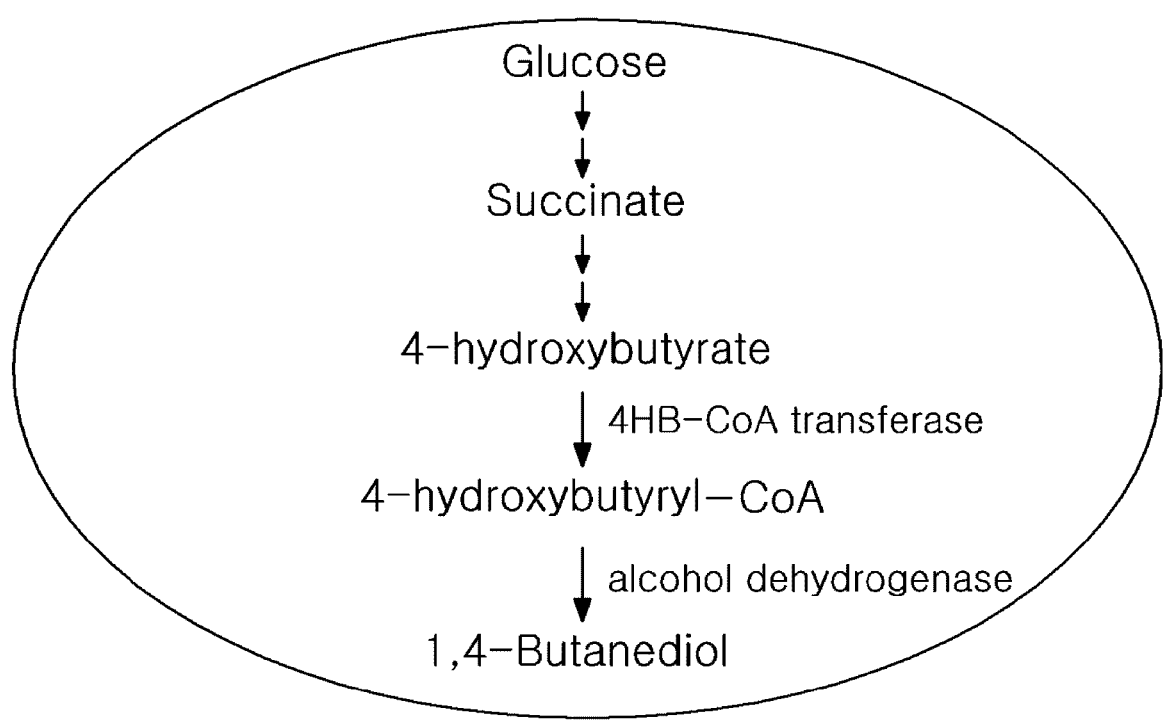
FIG. 2 a schematic diagram of a pathway for producing 1,4-butanediol through 4-hydroxybutyrate produced from succinate.

Hereinafter, the present invention will be described in more detail through examples. It will be clearly understood by those skilled in the art that the examples are provided merely to explain the present invention, not to limit its scope.

While, in the present invention, a method of preparing 1,4-butanediol uses Lumen bacteria such as mutants *Mannheimia* sp. LPK (KCTC 10558BP), LPK7 and LPK4, which have an inactive gene derived from a *Mannheimia* sp. strain and produce succinate in high concentration, *E. coli* and mutant *E. coli* W3110GFA, it will be also clearly understood by those skilled in the art that 1,4-butanediol may be produced by yielding a mutant producing succinate in high concentration using another Lumen bacteria strain, and introducing and amplifying a gene associated with producing 1,4-butanediol.

Further, while the following example provides a specific medium and culture method, it will be clearly understood by those skilled in the art that, as disclosed in the literatures (Lee et al., *Bioprocess Biosyst. Eng.*, 26:63, 2003; Lee et al., *Appl. Microbiol. Biotechnol.*, 58:663, 2002; Lee et al., *Biotechnol. Lett.*, 25:111, 2003; Lee et al., *Appl. Microbiol. Biotechnol.*, 54:23, 2000; and Lee et al., *Biotechnol. Bioeng.*, 72:41, 2001), a medium used herein may be different from a hydrolysate such as whey or corn steep liquor, or various culture methods such as fed-batch culture and continuous culture may be used.

EXAMPLE 1

Method of Preparing Microorganism Exhibiting High Production of Succinate 1-1. Preparation of Lumen Bacteria Having High Production of Succinate A microorganism, a Lumen bacterium, exhibiting high production of succinate according to the present invention was prepared by the method disclosed in PCT Publication No. WO 2005/052135. That is, a mutant strain *Mannheimia* sp. LPK (KCTC 10558BP) was prepared by inactivating a gene of lactate dehydrogenase (ldhA) and a gene of pyruvate-formate lyase (pfl) in *Mannheimia succiniciproducens* 55E, which is one of the Lumen bacteria species, and mutant strains (*Mannheimia* sp. LPK7 and LPK4) were prepared by inactivating a gene of phosphotransacetylase (pta), a gene of acetate kinase (ackA) and a gene of phosphopyruvate carboxylase (ppc) in the LPK strain.

1-2. Preparation of *E. Coli* Exhibiting High Production of Succinate

A microorganism, *E. coli*, exhibiting high production of succinate according to the present invention was prepared by the method disclosed in Korean Patent Publication No. 10-2006-0011345. That is, a mutant *E. coli* strain W3110GFA was yielded by inactivating a gene encoding glucose phototransferase (ptsG) and two genes encoding pyruvate kinase (pykA and pykF) in W3110 strain, which was transformed with a recombinant expression vector pTrcEBG expressing a bacteriophage red operon (exo-beta-gam).

EXAMPLE 2

Cloning of 1,4-Butanediol Converting Enzyme 2-1. Cloning of Genes Encoding 4-Hydroxybutyrate Converting Enzymes (Cat1, SucD and 4hbD)

The present inventors amplified cat1, sucD and 4hbD genes by polymerase chain reaction (PCR) using oligonucleotide primers synthesized based on a known gene sequence (L21902) in order to clone operons for genes encoding Cat1, SucD and 4hbD derived from *Clostridium kluyveri* DSM 555. The primers used for PCR were as follows.

SEQ ID NO 12: Cat1f-SacI
5'-tttcccgagctc TGTGAGGCGATTAAATGAGTAAAGGGATAAAG

SEQ ID NO 13: 4hbDb-XabI
gc tctaga tta gat aaa aaa gag gac att tca caa tat gg

To construct expression vector pTacLac4HB1, the operon for the amplified cat1, sucD and 4hbD genes were inserted into expression vector pTacLacI, which was cleaved with SacI/XbaI. The vector pTacLacI was constructed by cleaving vector pTac99A (Park and Lee, *J. Bacteriol.* 185, 5391-5397, 2003) with SspI, and ligating the cleaved vector with pTrc991 (Amersham Pharmacia Biotech), which was also cleaved with SspI. The vector pTacLacI has the same sequence as pTrc99A, and loses an NcoI restriction enzyme recognition site (restriction site) present in the pTrc99A from Multi Cloning sites (MCS). Here, the MCS started with an EcoRI site.

2-2. Cloning of Gene Encoding DctA Associated With Transport of Succinate

To clone a gene encoding DctA associated with transport of succinate in *E. coli* W3110, a DctA gene was amplified by DNA-PCR using oligonucleotide primers synthesized based on a known gene sequence (NC_000913). The primers used for PCR were as follows.

```
SEQ ID NO 14: DctAf-EcoRI
ggaattc ATGAAAACCTCTCTGTTTAAAAGC

SEQ ID NO 15: DctAb-XbaI
gc tctaga tta aga gga taa ttc gtg cgt ttt gcc
```

To construct expression vector p10499DctA, the amplified DctA gene was cleaved with EcoRI/XbaI and then inserted into expression vector p10499A (Park et al. (2002) FEMS Microbiol. Lett 214:217-222).

2-3. Cloning of Gene Encoding Enzyme Converting 4-Hydroxybutyrate into 1,4-Butanediol To clone genes encoding butyl-CoA dehydrogenase of SEQ ID NOs: 8 and 9, which are enzymes converting butyric acid into butanol in *Clostridium acetobutylicum*, cap0035 and cap0162 genes were amplified by DNA-PCR using oligonucleotide primers synthesized based on a known gene sequence (NC_003030). The primers used for PCR were as follows.

```
SEQ ID NO: 16: CAP0035f-SacI
tttcccgagctc atgaaagttacaaatcaaaaa

SEQ ID NO: 17: CAP0035b-XbaI
gc tctaga tta aaa tgc ttt tat ata gat

SEQ ID NO: 18: CAP0162f-EcoRI
GGA ATT C atgaaagtcacaacagtaaag

SEQ ID NO: 19: CAP0162b-XbaI
gc tctaga tta agg ttg ttt ttt aaa
```

To construct expression vectors pTacLacCAP35 and pTacLacCAP162, the amplified cap0035 and cap0162 genes were independently inserted into expression vectors pTacLacI, which were cleaved with SacI/XbaI and EcoRI/XbaI.

To convert 4-hydroxybutyrate into 4-hydroxybutyrate-CoA, an operon of a Cat2 gene of SEQ ID NO: 5 was amplified by DNA-PCR using oligonucleotide primers synthesized based on the sequence of SEQ ID NO: 5. The primers for PCR were as follows.

```
SEQ ID NO: 20: cat2f-EcoRI
ggaattc ATGGAGTGGGAAGAGATATATAAAGAG

SEQ ID NO: 21: cat2b-BamHI
cg ggatcc tta aaa tct ctt ttt aaa ttc att
cat taa tg
```

To construct expression vector pTacLacCat2, the amplified cat2 gene was inserted into expression vector pTacLacI, which was cleaved with EcoRI/BamHI.

To convert 4-hydroxybutyrate into 4-hydroxybutyrate-CoA, operons for ptb and buk genes of SEQ ID NOs: 6 and 7 were amplified by DNA-PCR using oligonucleotide primers synthesized based on the sequences of SEQ ID NOs: 6 and 7. The primers used for PCR were as follows.

```
SEQ ID NO: 22: ptbf-RcoRI
ggaattc ATGATTAAGAGTTTTAATGAAATATCATG

SEQ ID NO: 23: bukb-XbaI
gc tctaga tta ttt gta ttc ctt agc ttt ttc
ttc tcc
```

To construct an expression vector, operons for the amplified ptb and buk genes were inserted into expression vector pTacLacI, which was cleaved with EcoRI/XbaI, thereby obtaining pTacLacPtbBuk. The vector pTacLacPtbBuk was cleaved with SspI to obtain a gene fragment including a tac promoter, the ptb and buk genes and a transcription terminator, and the gene fragment was inserted into vector pBBR1MCS2 (Kovach et al., Gene. 166:175, 1995) which was cleaved with EcoRV, thereby obtaining vector pMCS2TacPtbBuk.

EXAMPLE 3

Yield of 1,4-BDO

Vectors pTacCAP162 and pMCS2Tacptbbuk were simultaneously transformed with *E. coli* XL1-Blue by electroporation and then plated on a LB plate containing 100 ug/ml ampicillin and 50 ug/ml kinamycin and cultured overnight at 37° C. The cultured colony was inoculated into a 15 ml tube (Falcon, USA) having 3 ml LB liquid medium containing 100 ug/ml ampicillin, and grown in a shaking incubator overnight at 200 rpm and 37° C. The incubated cells were inoculated into a fresh LB liquid medium containing 100 ml of 2% glucose and 100 ug/ml ampicillin, and then grown in a shaking incubator at 200 rpm and 37° C. When $OD_{600}$ reached 0.7, IPTG was added at a final concentration of 1 mM to induce protein expression and the cells were cultured overnight.

Figure 3:
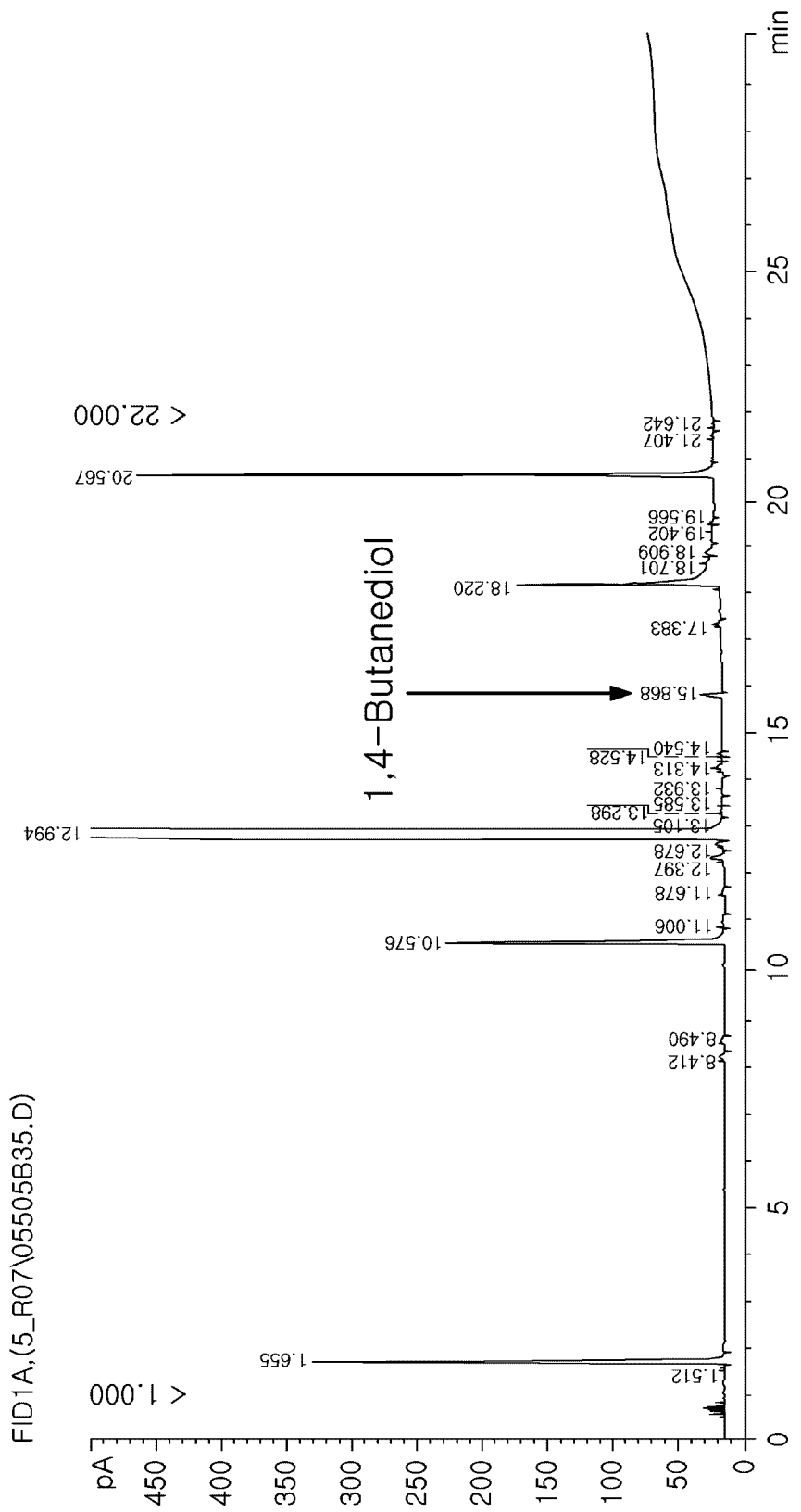
FIG. 3 shows GC analysis results of production of 1,4-butanediol.

Afterward, the culture was centrifuged and the supernatant was removed therefrom. Then, the cell pellet was washed with an MR medium once, resuspended in an MR medium containing 50 ml of 2% glucose, and 2% gamma-hydroxbutyrolactone and 1 mM IPTG, and fuzzed using gas mixture of 5% $H_2$, 5% $CO_2$ and $N_2$ balance for 30 minutes to set up an anaerobic condition. The culture was grown in a shaking incubator overnight for about 3 days at 200 rpm and 37° C., and then centrifuged to obtain a supernatant. The obtained supernatant was concentrated two times, and used as a GC analysis sample for analysis to confirm production of 1,4-butanediol. The analysis was conducted under the following conditions, and the results are shown in FIG. 3.

Column: AT-Waw (0.53 mm ID×15 ml, 1.2 um u.f. capillary)

Gas Flow Rate: Column (He): 4.0 ml/min

Oven Temperature Initial Value & Time: 50° C., 5 min

Program Rate: 10° C./min

Final Value & Time: 250° C., 5 min

Injector Temperature: 250° C.

Detector Temperature: 250° C.

Injector Split Ratio: 20/1

Injector Volume: 1.0 ul

As shown in FIG. 3, it was confirmed that 1,4-butanediol was produced.

While the invention has been shown and described with reference to certain examples thereof, it will be understood by those skilled in the art that various changes in form and details may be made therein without departing from the spirit and scope of the invention as defined by the appended claims.

The invention claimed is:

1. An isolated mutant microorganism exhibiting high production of 1,4-butanediol, which is prepared by introducing or amplifying genes encoding enzymes converting succinate into 4-hydroxybutyrate, and 4-hydroxybutyrate into 1,4-butanediol, in an *E. coli* capable of producing succinate, wherein the *E. coli* has inactive genes encoding glucose phosphotransferase (ptsG) and pyruvate kinase (pykA and pykF), and produces succinate in high concentration without substantial production of other organic acids in anaerobic condition,
wherein the gene encoding the enzyme converting succinate into 4-hydroxybutyrate is selected from the group consisting of genes encoding succinyl-CoA transferase (Cat 1), succinate semialdehyde dehydrogenase (SucD), 4-hydroxybutyrate dehydrogenase (4hbD) and 4-hydroxybutyrate dehydrogenase (GHB).

2. The isolated mutant microorganism according to claim 1, wherein the *E. coli* mutant is W3110GFA.

3. The isolated mutant microorganism according to claim 1, wherein the gene encoding the enzyme converting succinate into 4-hydroxybutyrate is isolated from *Clostridium kluyveri*.

4. The isolated mutant microorganism according to claim 1, wherein the gene encoding Cat 1 has a nucleotide sequence of SEQ ID NO: 1, the gene encoding SucD has a base sequence of SEQ ID NO: 2, the gene encoding 4hbD has a base sequence of SEQ ID NO: 3, and the gene encoding GHB has a base sequence of SEQ ID NO: 4.

5. The isolated mutant microorganism according to claim 1, wherein the mutant comprises a gene encoding Cat 1; a gene encoding SucD; and a gene encoding 4hbD or a gene encoding GHB.

6. The isolated mutant microorganism according to claim 1, wherein the gene encoding the enzyme converting 4-hydroxybutyrate into 1,4-butanediol is isolated from *Clostridium acetobutylicum*.

7. The isolated mutant microorganism according to claim 1, wherein the gene encoding the enzyme converting 4-hydrxoybutyrate into 1,4-butanediol is a gene encoding 4-hydroxybutyrate-CoA transferase and a gene encoding alcohol dehydrogenase reducing 4-hydroxybutyrate-CoA; or a gene encoding phosphotransbutyrylase, a gene encoding butyryl kinase and a gene encoding alcohol dehydrogenase reducing 4-hydroxybutyrate-CoA.

8. The isolated mutant microorganism according to claim 7, wherein the gene encoding 4-hydroxybutyrate-CoA transferase has a nucleotide sequence of SEQ ID NO: 5.

9. The isolated mutant microorganism according to claim 7, wherein the gene encoding phosphotransbutyrylase and the gene encoding butyryl kinase have nucleotide sequences of by SEQ ID NOs: 6 and 7, respectively.

10. The isolated mutant microorganism according to claim 7, wherein the alcohol dehydrogenase is butyl-CoA dehydrogenase isolated from *Clostridium acetobutylicum*.

11. The isolated mutant microorganism according to claim 10, wherein the gene encoding butyl-CoA dehydrogenase has a nucleotide sequence of SEQ ID NO: 8 or 9.

12. The isolated mutant microorganism according to claim 1, wherein the mutant has an inactive gene associated with conversion of succinate semialdehyde into succinate.

13. The isolated mutant microorganism according to claim 12, wherein the gene associated with conversion of succinate semialdehyde into succinate is a gene encoding succinic semialdehyde dehydrogenase (GabD).

14. The isolated mutant microorganism according to claim 13, wherein the gene encoding GabD has a nucleotide sequence of SEQ ID NO: 10.

15. The isolated mutant microorganism according to claim 1, wherein a gene encoding C4-dicarboxylate transport protein (DctA) associated with transport of succinate is further introduced or amplified in the mutant.

16. The isolated mutant microorganism according to claim 15, wherein the gene encoding DctA has a nucleotide sequence of SEQ ID NO: 11.

17. An isolated mutant microorganism exhibiting high production of 1,4-butanediol, which is prepared by introducing or amplifying a gene encoding Cat1; a gene encoding SucD; a gene encoding 4hbD or GHB; a gene encoding 4-hydroxybutyrate-CoA transferase, or a gene encoding Ptb (phosphotransbutyrylase) and a gene encoding Buk (Butyrylkinase); and a gene encoding butyl-CoA dehydrogenase, in *E. coli*, having inactive genes encoding glucose phosphotransferase (ptsG) and pyruvate kinase (pvkA and pvkF), capable of producing succinate in high concentration in anaerobic condition.

18. The isolated mutant microorganism according to claim 17, wherein a gene encoding GabD is inactivated in the mutant microorganism.

19. The isolated mutant microorganism according to claim 17, wherein a gene encoding DctA associated with transport of succinate is introduced or amplified in the mutant microorganism.

20. A method of preparing 1,4-butanediol, comprising:
culturing the mutant microorganism according to claim 1 in a medium containing a carbon source; and
obtaining 1,4-butanediol from the medium.

* * * * *